(12) United States Patent
Salazar et al.

(10) Patent No.: US 11,622,805 B2
(45) Date of Patent: Apr. 11, 2023

(54) APPARATUS AND METHOD FOR PERFORMING VIDIAN NEURECTOMY PROCEDURE

(71) Applicant: Acclarent, Inc., Irvine, CA (US)

(72) Inventors: Henry F. Salazar, Pico Rivera, CA (US); John H. Thinnes, Jr., Mission Viejo, CA (US); Jetmir Palushi, Irvine, CA (US); Martin J. Citardi, Houston, TX (US)

(73) Assignee: Acclarent, Inc., Irvine, CA (US)

( * ) Notice: Subject to any disclaimer, the term of this patent is extended or adjusted under 35 U.S.C. 154(b) by 750 days.

(21) Appl. No.: 16/003,438

(22) Filed: Jun. 8, 2018

(65) Prior Publication Data

US 2019/0374280 A1  Dec. 12, 2019

(51) Int. Cl.
*A61B 18/14* (2006.01)
*A61B 34/20* (2016.01)
(Continued)

(52) U.S. Cl.
CPC .......... *A61B 18/1477* (2013.01); *A61B 34/20* (2016.02); *A61B 90/03* (2016.02);
(Continued)

(58) Field of Classification Search
CPC .......... A61B 17/24; A61B 2018/00327; A61B 2018/00434; A61B 2018/00571;
(Continued)

(56) References Cited

U.S. PATENT DOCUMENTS 5,792,135 A  8/1998 Madhani et al.
5,817,084 A  10/1998 Jensen
(Continued)

FOREIGN PATENT DOCUMENTS

WO  WO 1999/032041 A1  7/1999
WO  WO 2011/005903 A2  1/2011
(Continued)

OTHER PUBLICATIONS

U.S. Appl. No. 15/695,520, entitled "Sensor Guided Instrument with Penetrating Feature," filed Sep. 5, 2017.
(Continued)

*Primary Examiner* — Ronald Hupczey, Jr.
*Assistant Examiner* — Bradford C. Blaise
(74) *Attorney, Agent, or Firm* — Frost Brown Todd LLP

(57) ABSTRACT

A surgical instrument includes a shaft and a probe that extends distally from a distal end of the shaft. The probe includes a distal tip configured to puncture a tissue surface to enter a nerve canal of a patient, and an ablation element operable to ablate a nerve located within the nerve canal. The surgical instrument further includes a stop element arranged proximally of the distal tip. The stop element is configured to abut the tissue surface punctured by the distal tip. In some examples, the ablation element may be in the form of an RF electrode operable to ablate the nerve with RF energy. The surgical instrument may further include a navigation sensor operable to generate a signal corresponding to a location of the probe within the patient.

11 Claims, 7 Drawing Sheets

(51) Int. Cl.
*A61B 90/00* (2016.01)
*A61B 34/10* (2016.01)
*A61B 18/00* (2006.01)
*A61B 17/24* (2006.01)

(52) U.S. Cl.
CPC ........... *A61B 17/24* (2013.01); *A61B 18/1485* (2013.01); *A61B 34/10* (2016.02); *A61B 2018/00327* (2013.01); *A61B 2018/00434* (2013.01); *A61B 2018/00577* (2013.01); *A61B 2018/00791* (2013.01); *A61B 2018/00839* (2013.01); *A61B 2034/105* (2016.02); *A61B 2034/2051* (2016.02); *A61B 2090/034* (2016.02)

(58) Field of Classification Search
CPC .. A61B 2018/00791; A61B 2018/1467; A61B 18/1477; A61B 18/1482; A61B 18/1485; A61B 34/20; A61B 2034/2051; A61B 90/03; A61B 2090/033; A61B 2090/034; A61B 2090/036
See application file for complete search history.

(56) References Cited

U.S. PATENT DOCUMENTS

| | | |
|---|---|---|
| 5,878,193 A | 3/1999 | Wang et al. |
| 6,109,268 A | 8/2000 | Thapliyal et al. |
| 6,231,565 B1 | 5/2001 | Tovey et al. |
| 6,361,531 B1 | 3/2002 | Hissong |
| 6,364,888 B1 | 4/2002 | Niemeyer et al. |
| 6,526,318 B1 | 2/2003 | Ansarinia |
| 6,783,524 B2 | 8/2004 | Anderson et al. |
| 7,524,320 B2 | 4/2009 | Tierney et al. |
| 7,691,098 B2 | 4/2010 | Wallace et al. |
| 7,720,521 B2 | 5/2010 | Chang et al. |
| 7,806,891 B2 | 10/2010 | Nowlin et al. |
| 8,123,722 B2 | 2/2012 | Chang et al. |
| 8,190,389 B2 | 5/2012 | Kim et al. |
| 8,320,711 B2 | 11/2012 | Altmann et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,702,626 B1 | 4/2014 | Kim et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,936,594 B2 | 1/2015 | Wolf et al. |
| 9,072,597 B2 | 7/2015 | Wolf et al. |
| 9,167,961 B2 | 10/2015 | Makower et al. |
| 9,198,736 B2 | 12/2015 | Kim et al. |
| 9,301,759 B2 | 4/2016 | Spivey et al. |
| 9,415,194 B2 | 8/2016 | Wolf et al. |
| 9,808,144 B2 | 11/2017 | Goldfarb et al. |
| 2003/0139789 A1 | 7/2003 | Tvinnereim et al. |
| 2004/0186469 A1 | 9/2004 | Woloszko et al. |
| 2004/0204747 A1 | 10/2004 | Kemeny et al. |
| 2005/0283148 A1 | 12/2005 | Janssen et al. |
| 2006/0004323 A1 | 1/2006 | Chang et al. |
| 2007/0208252 A1 | 9/2007 | Makower |
| 2009/0149849 A1 | 6/2009 | Lin et al. |
| 2010/0030031 A1 | 2/2010 | Goldfarb et al. |
| 2010/0274164 A1 | 10/2010 | Juto |
| 2011/0004057 A1 | 1/2011 | Goldfarb et al. |
| 2011/0060214 A1 | 3/2011 | Makower |
| 2013/0281967 A1* | 10/2013 | Papay ................ A61B 18/1477 604/512 |
| 2013/0317339 A1 | 11/2013 | Waldstreicher et al. |
| 2013/0324989 A1 | 12/2013 | Leung et al. |
| 2014/0200444 A1 | 7/2014 | Kim et al. |
| 2014/0364725 A1 | 12/2014 | Makower |
| 2015/0164571 A1* | 6/2015 | Saadat ............... A61B 18/1485 600/109 |
| 2015/0351831 A1* | 12/2015 | Janssen .............. A61B 18/1477 606/42 |
| 2016/0008083 A1 | 1/2016 | Kesten et al. |
| 2016/0310041 A1 | 10/2016 | Jenkins et al. |
| 2016/0310042 A1 | 10/2016 | Kesten et al. |
| 2016/0331459 A1 | 11/2016 | Townley et al. |
| 2018/0103994 A1 | 4/2018 | Fox et al. |

FOREIGN PATENT DOCUMENTS

| | | |
|---|---|---|
| WO | WO 2011/025830 A1 | 3/2011 |
| WO | WO 2015/048806 A2 | 4/2015 |

OTHER PUBLICATIONS

U.S. Appl. No. 15/797,049, entitled "Dilation Catheter with Navigation Sensor and Vent Passageway in Tip," filed Oct. 30, 2017.
U.S. Appl. No. 15/797,091, entitled "Suction Device with Bipolar RF Cuff," filed Oct. 30, 2017.
U.S. Appl. No. 15/923,164, entitled "Navigation Instrument with Obliquely Oriented Sensing Coil," filed Mar. 19, 2018.
U.S. Appl. No. 15/933,737, entitled "Apparatus to Secure Field Generating Device to Chair," filed Mar. 23, 2018.
International Search Report and Written Opinion dated Jan. 8, 2020 for Application No. PCT/IB2019/054771, 18 pgs.
Fukutake, Tomoshige, et al. "Laser surgery for allergic rhinitis." *Archives of Otolaryngology—Head & Neck Surgery* 112.12 (1986): 1280-1282.
Gindros, George, et al. "Mucosal changes in chronic hypertrophic rhinitis after surgical turbinate reduction." *European archives of oto-rhino-laryngology* 266.9 (2009): 1409-1416.
Ho, Ki-Hong Kevin, et al. "Electromechanical reshaping of septal cartilage." *The Laryngoscope* 113.11 (2003): 1916-1921.

* cited by examiner

APPARATUS AND METHOD FOR PERFORMING VIDIAN NEURECTOMY PROCEDURE

BACKGROUND

Rhinitis is a medical condition that presents as irritation and inflammation of the mucous membrane within the nasal cavity. The inflammation results in the generation of excessive amounts of mucus, which can cause runny nose, nasal congestion, sneezing, and/or post-nasal drip. Allergenic rhinitis is an allergic reaction to environmental factors such as airborne allergens, while non-allergenic (or "vasomotor") rhinitis is a chronic condition that presents independently of environmental factors. Conventional treatments for rhinitis include antihistamines, topical or systemic corticosteroids, and topical anticholinergics, for example.

For cases of intractable rhinitis in which the symptoms are severe and persistent, an additional treatment option is the surgical removal of a portion of the vidian (or "pterygoid") nerve, a procedure known as vidian neurectomy. The theoretical basis for vidian neurectomy is that rhinitis is caused by an imbalance between parasympathetic and sympathetic innervation of the nasal cavity, and the resultant over stimulation of mucous glands of the mucous membrane. Vidian neurectomy aims to disrupt this imbalance and reduce nasal mucus secretions via surgical treatment of the vidian nerve. However, conventional surgical instruments and procedures for performing vidian neurectomies are known to cause undesirable degrees of trauma to patient tissue and yield inconsistent results.

FIG. 1 depicts a left sagittal view of a portion of a patient's head, showing the nasal cavity (10), the frontal sinus (12), the sphenoid sinus (14), and the sphenoid bone (16). The nasal cavity (10) is bounded laterally by the nasal wall (18), which includes an inferior turbinate (20), a middle turbinate (22), and a superior turbinate (24). The vidian nerve (32) resides within the vidian (or "pterygoid") canal (30), which is defined in part by the sphenoid bone (16) and is located posterior to the sphenoid sinus (14), approximately in alignment with the middle turbinate (22). The vidian nerve (32) is formed at its posterior end by the junction of the greater petrosal nerve (34) and the deep petrosal nerve (36), and joins at its anterior end with the pterygopalatine ganglion (38), which is responsible for regulating blood flow to the nasal mucosa.

While instruments and methods for performing vidian neurectomies are known, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
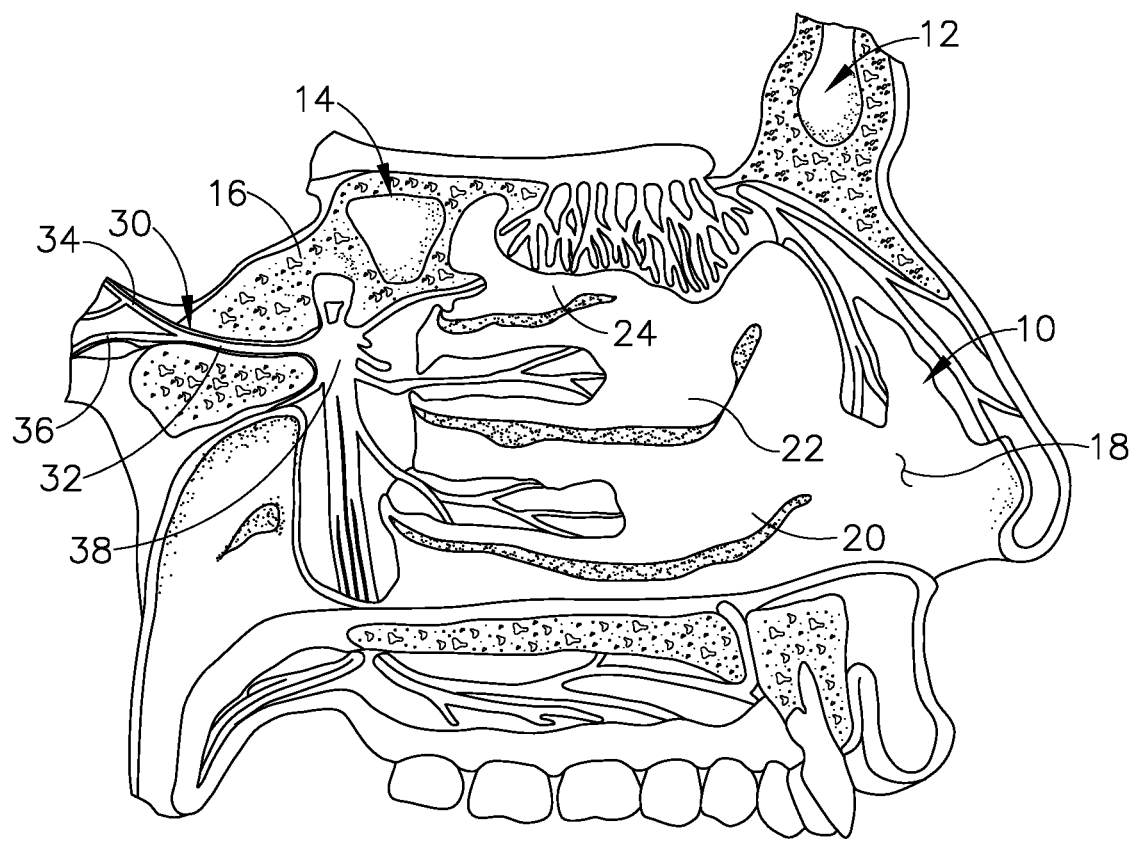
FIG. 1 depicts a left sagittal view of a portion of a patient's head, showing details of certain paranasal sinuses and nerves, including the vidian nerve.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal"

refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Surgical Navigation System with Vidian Neurectomy Surgical Instrument A. Overview of Surgery Navigation System Image-guided surgery (IGS) is a technique in which a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., crosshairs, illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

An example of an electromagnetic IGS system that may be used in ENT and sinus surgery is the CARTO® 3 System by Biosense-Webster, Inc., of Irvine, Calif. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of medical procedures where anatomical landmarks are not present or are difficult to visualize endoscopically.

Figure 2:
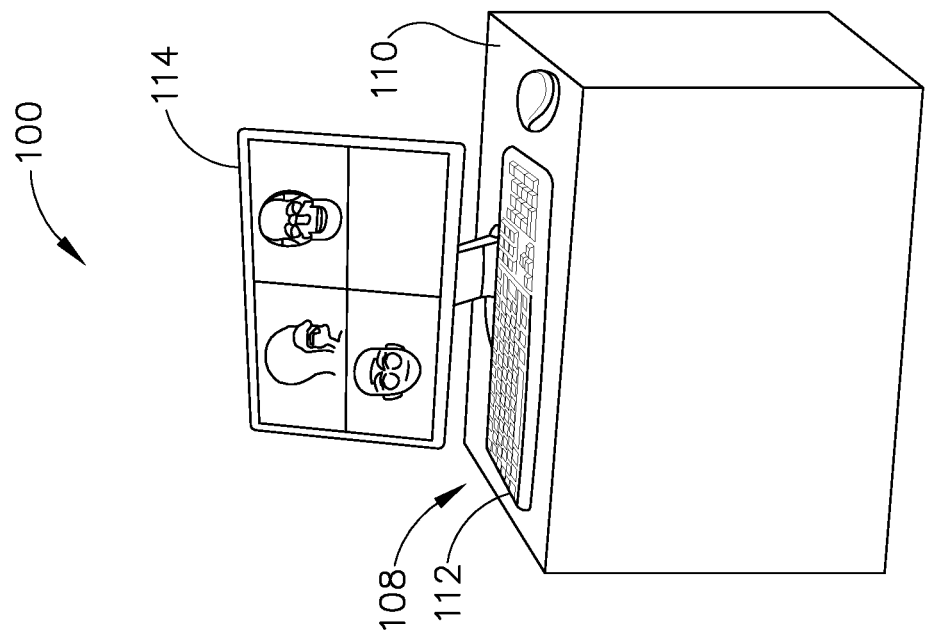
FIG. 2 depicts a schematic perspective view of an exemplary surgical navigation system being used to perform a surgical procedure on a patient seated in a medical procedure chair.
Figure 2:
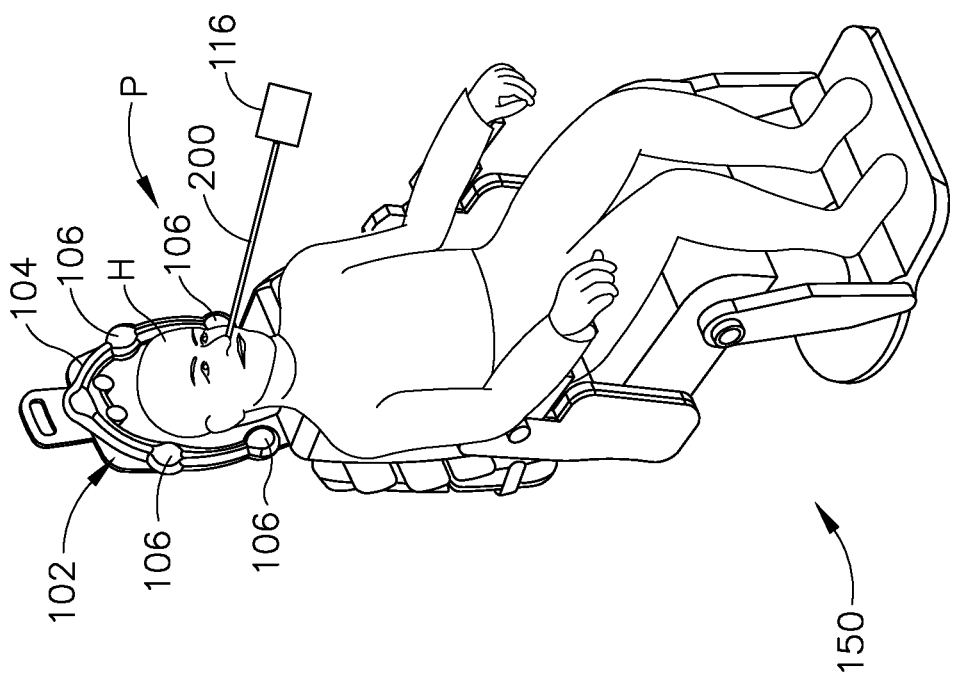

FIG. 2 shows an exemplary surgical navigation system (100) equipped with IGS components that enable a medical procedure to be performed on a patient (P) using image guidance. As described in greater detail below, surgical navigation system (100) of the present example includes a surgical instrument (200) operable to perform a vidian neurectomy procedure on patient (P), and which includes a navigation sensor (240) that enables tracking of a distal end of instrument (200) within patient (P) during a procedure. In other examples, surgical navigation system (100) may include one or more other types of surgical instruments operable to perform various other types of surgical procedures on patient (P). For instance, surgical navigation system (100) may include a dilation instrument operable to dilate the ostium of a paranasal sinus of patient (P); or to dilate some other anatomical passageway (e.g., within the ear, nose, or throat, etc.). In that regard, surgical navigation system (100) may be used to perform various kinds of medical procedures within the patient's head (H), including but not limited to within the nasal cavity, paranasal sinuses, Eustachian tubes, etc.; within the patient's throat; or elsewhere within the patient's body. Various suitable locations and clinical contexts in which surgical navigation system (100) may be used will be apparent to those of ordinary skill in the art in view of the teachings herein.

Surgical navigation system (100) of the present example includes a field generator assembly (102), which comprises a set of electromagnetic field generators (106) that are integrated within a horseshoe-shaped frame (104) configured to be positioned about head (H) of patient (P). Field generators (106) are operable to generate alternating magnetic fields of different frequencies around the patient's head (H). Field generators (106) thereby enable tracking of the position of a navigation instrument, such as surgical instrument (200), that is inserted into the patient's head (H). Various suitable components that may be used to form and drive field generators (106) will be apparent to those of ordinary skill in the art in view of the teachings herein.

In the present example, frame (104) is mounted to the headrest of a medical procedure chair (150), with patient (P) being seated in chair (150) such that frame (104) is located adjacent to the patient's head (H). By way of example only, chair (150) and/or field generator assembly (102) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561, 370 on Feb. 18, 2020, the disclosure of which is incorporated by reference herein. In other examples, patient (P) may be supported on a variety of other suitable support structures, such as a medical procedure table, and frame (104) may be supported by the patient support structure or by an independent structure positioned adjacent to the patient support structure. In other examples, frame (104) may be secured directly to the patient's head (H).

Surgical navigation system (100) further includes a processor (108) that communicates with one or more memories and is operable to control field generators (106) and other elements of navigation system (100). For instance, processor (108) is operable to drive field generators (106) to generate an alternating electromagnetic field, and process signals received from navigation sensor (240) arranged within a distal end of surgical instrument (200) (see FIG. 5). As described in greater detail below, navigation sensor (240) is operable to generate signals that correspond to a location of the distal end of surgical instrument (200) within patient (P) in response to the presence of sensor (240) within the alternating electromagnetic field generated about patient (P) by field generators (106). Processor (108) receives these signals and executes an algorithm to calculate location coordinates of the distal end of surgical instrument (200). In this manner, processor (108) cooperates with navigation sensor (240) to track a location of the distal end of surgical instrument (200) within patient (P) in real time during a medical procedure.

As shown in FIG. 2, processor (108) of the present example is mounted in a console (110), which comprises operating controls (112) that include a keypad and/or a pointing device such as a mouse or trackball. A physician uses operating controls (112) to interact with processor (108) while performing the surgical procedure. Processor (108) uses software stored in a memory of processor (108) to calibrate and operate system (100). Such operation includes driving field generators (106), processing data received from navigation sensor (240), processing data from operating controls (112), and driving a display device (114), shown in the form of a screen. The software may be downloaded to processor (108) in electronic form, over a network, for example, or it may, alternatively or additionally, be provided and/or stored on non-transitory tangible media, such as magnetic, optical, or electronic memory.

Figure 5:
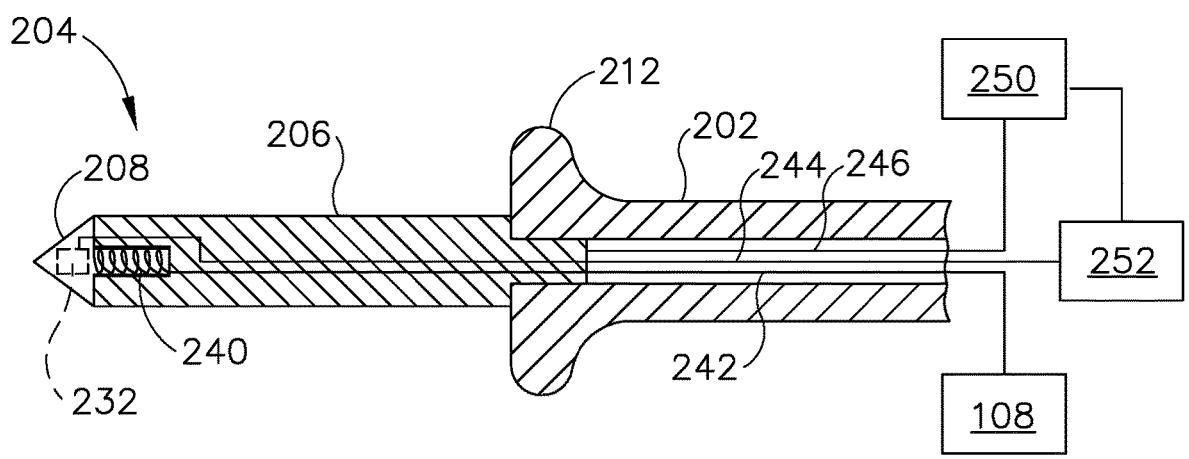
FIG. 5 depicts a schematic side sectional view of the distal portion of the surgical instrument of FIG. 4, showing internal features of the instrument including a navigation sensor and a nerve sensor.

Surgical instrument (200), including its navigation sensor (240), communicates with processor (108) via a communication unit (116) coupled with a proximal end of surgical instrument (200), as shown in FIG. 5. Communication unit (116) of the present example is configured to provide wireless communication of data and other signals between console (110) and surgical instrument (200). In some versions, communication unit (116) simply communicates data or other signals from surgical instrument (200) to console (110) uni-directionally, without also communicating data or other signals from console (110). In some other versions, communication unit (116) provides bi-directional communication of data or other signals between surgical instrument (200) and console (110). While communication unit (116) of the present example couples with console (110) wirelessly, some other versions may provide wired coupling between communication unit (116) and console (110). Various other suitable features and functionality that may be incorporated into communication unit (116) will be apparent to those of ordinary skill in the art in view of the teachings herein.

Processor (108) is further operable to provide video in real time via display (114), showing the position of the distal end of surgical instrument (200) in relation to a video camera image of the patient's head (H), a CT scan image of the patient's head (H), and/or a computer generated three-dimensional model of the anatomy within and adjacent to the patient's nasal cavity (10). Display (114) may display such images simultaneously and/or superimposed on each other during the surgical procedure. Such displayed images may also include graphical representations of instruments that are inserted in the patient's head (H), including surgical instrument (200), such that the operator may view the virtual rendering of the instrument at its actual location in real time. By way of example only, display (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display (114).

Any suitable device may be used to generate a three-dimensional model of the internal anatomy of patient (P) about which the electromagnetic field is generated and into which surgical instrument (200) is inserted during a surgical procedure. By way of example only, such a model may be generated in accordance with at least some of the teachings of U.S. Pat. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional anatomical model may be generated will be apparent to those of ordinary skill in the art in view of the teachings herein. It should also be understood that, regardless of how or where the three-dimensional model is generated, the model may be stored on console (110). Console (110) may thus render images of at least a portion of the model via display (114), and further render real-time video images of the position of distal end of surgical instrument (200) in relation to the model via display (114).

In various examples, surgical navigation system (100) may be further configured in accordance with one or more teachings of U.S. patent application Ser. No. 15/695,520, entitled "Sensor Guided Instrument with Penetrating Feature," filed Sep. 5, 2017issued as U.S. Pat. No. 10,835,327 on Nov. 17, 2020; U.S. patent application Ser. No. 15/797, 049, entitled "Dilation Catheter with Navigation Sensor and Vent Passageway in Tip," filed Oct. 30, 2017, issued as U.S. Pat. No. 10,736,647 on Aug. 11, 2020; U.S. Pat. No. 8,702,626, entitled "Guidewires for Performing Image Guided Procedures," issued Apr. 22, 2014; U.S. Pat. No. 8,320,711, entitled "Anatomical Modeling from a 3-D Image and a Surface Mapping," issued Nov. 27, 2012; U.S. Pat. No. 8,190,389, entitled "Adapter for Attaching Electromagnetic Image Guidance Components to a Medical Device," issued May 29, 2012; U.S. Pat. No. 8,123,722, entitled "Devices, Systems and Methods for Treating Disorders of the Ear, Nose and Throat," issued Feb. 28, 2012; U.S. Pat. No. 7,720,521, entitled "Methods and Devices for Performing Procedures within the Ear, Nose, Throat and Paranasal Sinuses," issued May 18, 2010; U.S. Pat. Pub. No. 2014/0364725, entitled "Systems and Methods for Performing Image Guided Procedures within the Ear, Nose, Throat and Paranasal Sinuses," published Dec. 11, 2014, now abandoned; U.S. Pat. Pub. No. 2014/0200444, entitled "Guidewires for Performing Image Guided Procedures," published Jul. 17, 2014, now abandoned; U.S. Pat. No. 9,198,736, entitled "Adapter for Attaching Electromagnetic Image Guidance Components to a Medical Device," issued Dec. 1, 2015; U.S. Pat. Pub. No. 2011/0060214, entitled "Systems and Methods for Performing Image Guided Procedures within the Ear, Nose, Throat and Paranasal Sinuses," published Mar. 10, 2011, now abandoned; U.S. Pat. No. 9,167,961, entitled "Methods and Apparatus for Treating Disorders of the Ear Nose and Throat," issued Oct. 27, 2015; and/or U.S. Pat. Pub. No. 2007/0208252, entitled "Systems and Methods for Performing Image Guided Procedures within the Ear, Nose, Throat and Paranasal Sinuses," published Sep. 6, 2007, now abandoned. The disclosure of each of these references is incorporated by reference herein.

B. Vidian Neurectomy Instrument with Navigational Probe

Figure 3:
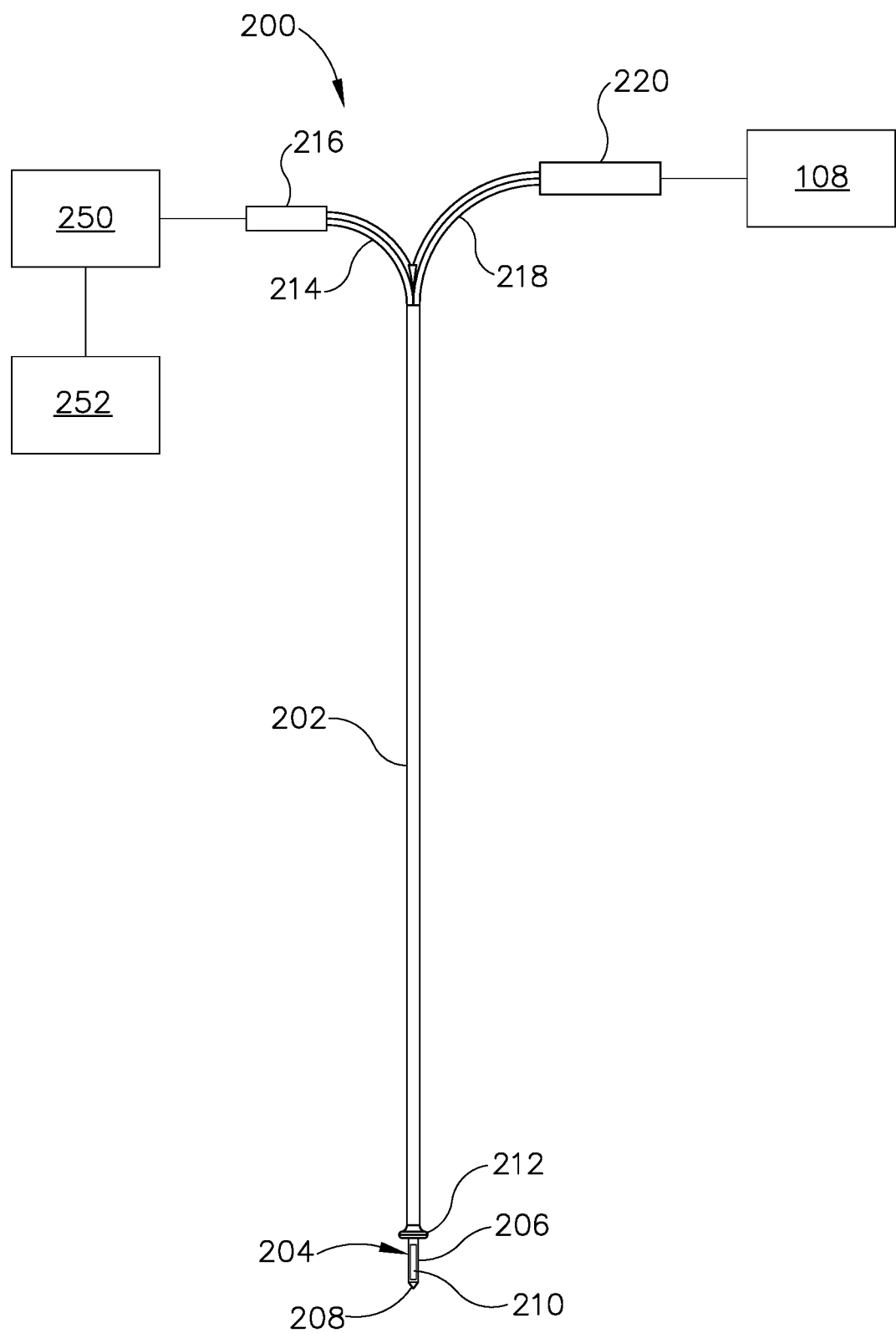
FIG. 3 depicts a schematic front elevational view of an exemplary vidian neurectomy surgical instrument of the surgical system of FIG. 2.

FIG. 3 shows an exemplary vidian neurectomy surgical instrument (200) configured for use with IGS surgical navigation system (100) described above. Surgical instrument (200) includes an elongate shaft (202) that extends along a longitudinal shaft axis. A probe (204) extends distally from a distal end of shaft (202) along the shaft axis. Probe (204) includes a cylindrical shank (206) and a sharpened distal tip (208) configured to puncture through tissue and a nerve channel as described in greater detail below. Probe (204) further includes an ablation element (210) arranged on shank (206) and configured to ablate a nerve arranged within the nerve channel, as described below. In some examples, probe (204) may be releasably connected to the distal end of shaft (202), such as by threaded engagement. Surgical instrument (200) further includes a stop element (212) in the form of an annular collar arranged at a distal end of shaft (202) and a proximal end of probe (204). Collar (212) may be formed integrally with the distal end of shaft (202) in some examples. Probe (204) may be fully rigid to promote puncturing of distal tip (208) through patient tissue during a surgical procedure. Shaft (202) may be fully or partially rigid to facilitate insertion of surgical instrument (200) into a patient's nasal cavity (10), and to suitably transfer to distal tip (208) a distally directed puncturing force applied by a surgeon to shaft (202) during the procedure.

As shown in FIG. 3, a first conduit (214) extends proximally from a proximal end of instrument shaft (202) and terminates at a first electrical connector (216) that is configured to couple with an ablation energy source (250), which communicates with an ablation system processor (252). Ablation system processor (252) is operable to control an amount of ablation energy directed from ablation energy source (250) to ablation element (210) of probe (204) for treatment of a nerve or other tissue during a surgical procedure. A second conduit (218) extends proximally from the proximal end of instrument shaft (202) and terminates at a second electrical connector (220) that is configured to communicate with navigation system processor (108) described above, for example via communication unit (116). In some examples, ablation system processor (252) and navigation system processor (108) may be may be one and the same and/or may be otherwise incorporated into the same unit of capital equipment. In other examples, ablation system processor (252) may be separate from but communicate directly with navigation system processor (108).

Figure 4:
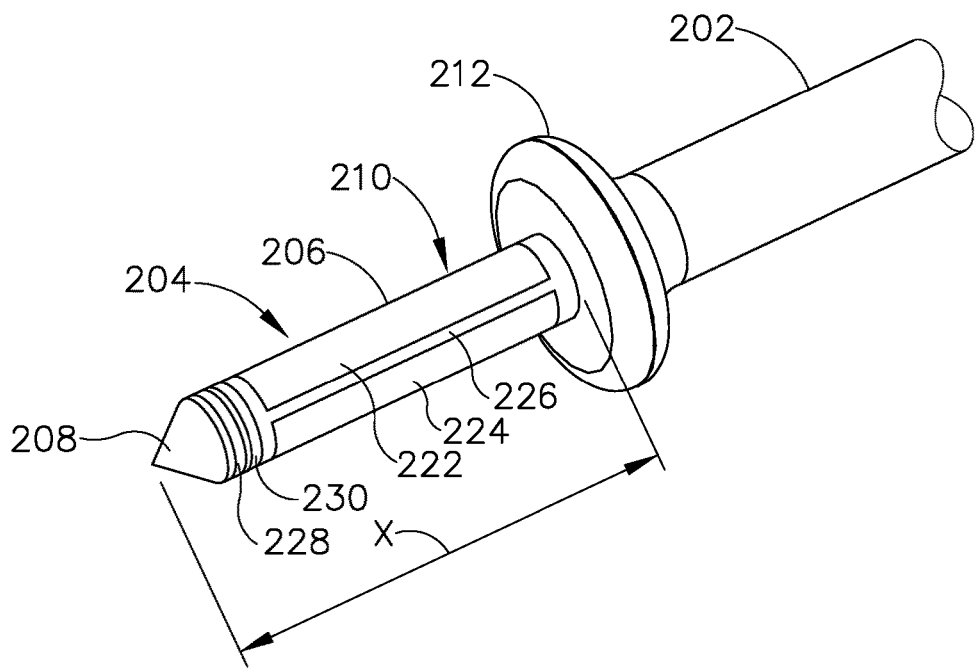
FIG. 4 depicts a perspective view of a distal portion of the surgical instrument of FIG. 3, showing details of a probe having an ablation element, and a stop collar at a proximal end of the probe.

FIGS. 4 and 5 show additional details of probe (204) and stop collar (212) of surgical instrument (200). In use, distal tip (208) of probe (204) punctures through a tissue surface that lines the wall of a nerve canal, such as vidian canal (30). Stop collar (212) is configured to abut the tissue surface as probe (204) is directed into the nerve canal, to thereby maintain probe ablation element (210) in engagement with the nerve housed in the nerve canal so the nerve may be ablated. Accordingly, stop collar (212) is positioned proximally from distal tip (208) by a distance (X) so as to provide probe (204) with a corresponding length (X) that suitably positions probe (204) within the nerve canal during use. In that regard, it will be appreciated that distance (X) may be sized based on the particular nerve and nerve canal being targeted. In the present example, surgical instrument (200) is configured to ablate vidian nerve (32) located within vidian canal (30). Accordingly, probe (204) and stop collar (212) of the present example are configured such that distance (X) suitably positions probe (204) and ablation element (210) within vidian canal (230) and in engagement with vidian nerve (32) during a vidian neurectomy procedure. For instance, probe (204) and stop collar (212) may be configured such that distance (X) is approximately 8 millimeters. It will be appreciated that in other examples distance (X) may be of various other suitable quantities readily apparent to those of ordinary skill in the art based on a particular application.

As shown in FIG. 5, ablation element (210) is provided in the form of a pair of RF electrodes (222, 224) operable to apply bipolar RF energy to a nerve positioned in contact with both electrodes (222, 224), to thereby ablate the nerve. Each RF electrode (222, 224) extends longitudinally for substantially a full length of probe shank (206), and circumferentially about a respective first or second half of shank (206). RF electrodes (222, 224) are spaced apart from one another circumferentially by an opposed pair of axially extending gaps (226) that prevent electrical shorting between RF electrodes (222, 224) in the absence of a nerve or other tissue positioned in electrical contact with RF electrodes (222, 224). First RF electrode (222) may function as an active electrode, and second RF electrode (224) may function as a return electrode. Further, in the present example, ablation energy source (250) is in the form of an RF energy source operable to deliver bipolar RF energy to RF electrodes (222, 224) at a power and for a duration as instructed by ablation system processor (252), which may be dictated by the surgeon via a suitable user interface (not shown). In other examples, ablation element (210) may be configured to deliver bipolar RF energy via three or more RF electrodes positioned circumferentially about probe shank (206), for example as disclosed in U.S. application Ser. No. 15/797,091, entitled "Suction Device With Bipolar RF Cuff," filed Oct. 30, 2017, now abandoned, the disclosure of which is incorporated by reference herein.

In further examples, ablation element (210) may be provided in various other forms suitable to ablate a nerve of a patient. For instance, though not shown, ablation element (210) may be in the form of a single RF electrode operable to apply monopolar RF energy to a nerve in combination with a ground pad positioned in contact with the patient's skin. Alternatively, or in addition, ablation element (210) may comprise a resistance heating device, a cryoablation applicator, a chemical applicator, and/or an optical energy transmission device. It will be appreciated that ablation energy source (250) may be suitably configured in such alternative examples to provide the corresponding ablation energy or medium to a nerve engaged by instrument probe (204) during a neurectomy procedure to thereby ablate the nerve.

Surgical instrument (200) may further include a nerve sensor configured to detect a condition of the nerve being treated by probe (204), and which communicates with ablation system processor (252). FIG. 4 shows a first exemplary nerve sensor in the form of a pair of annular detection electrodes (228, 230) positioned at a distal end of probe shank (206). Detection electrodes (228, 230) are spaced axially from one another and are operable to deliver a low-power neuro-stimulating signal to a nerve positioned in contact with detection electrodes (228, 230) to thereby detect presence of the nerve. In that regard, first detection electrode (228) is operable as a transmitting electrode and second detection electrode (230) is operable as a receiving electrode. Throughout ablation of a nerve, detection electrodes (228, 230) may be activated to deliver the stimulating signal to the nerve. As long as the nerve remains substantially intact and unablated so as to contact both detection electrodes (228, 230) simultaneously, the neuro-stimulating signal will pass from first electrode (228) to second electrode (230) via the nerve, thereby indicating to ablation system processor (252) that the nerve is at least partially intact and thus not yet fully ablated. Once the nerve has been fully ablated, the neuro-stimulating signal will no longer pass through the nerve to second detection electrode (230), and thus ablation system processor (252) will detect that nerve ablation is complete.

In some examples, detection electrodes (228, 230) may be omitted and RF electrodes (222, 224) may be operable to ablate a nerve with high-power levels of RF energy, and to detect the condition of the nerve with low-power levels of RF energy. For instance, RF electrodes (22, 224) may be operable to deliver a neuro-stimulating signal to the nerve being ablated in a manner similar to detection electrodes (228, 230) described above. Such a signal may be delivered simultaneously or in a rapidly alternating fashion with RF ablation energy. In some examples, RF electrodes (22, 24), or alternatively detection electrodes (228, 230), may be employed to track the electrical impedance of the nerve using various methods and components readily apparent to those of ordinary skill in the art. For instance, upon the detected impedance reaching a threshold value, ablation system processor (252) may determine that nerve ablation is complete and subsequently deactivate RF electrodes (22, 24) to cease delivery of ablation energy.

FIG. 5 depicts a side sectional view showing additional features of surgical instrument (200), including a second exemplary nerve sensor in the form of a temperature sensor (232) arranged within distal tip (208) of probe (204). Temperature sensor (232) may be arranged within probe shank (206) in other examples. Temperature sensor (232) is operable to detect a temperature of a nerve being treated with ablation energy, such as bipolar RF energy, by ablation element (210). Temperature sensor (232) communicates with ablation system processor (252), which is configured to monitor a temperature of the nerve as indicated by temperature sensor (232) throughout ablation to determine when the nerve has been fully ablated. For instance, processor (252) may determine that the nerve has been fully ablated once the detected temperature rises to a predetermined degree. Temperature sensor (232) may be provided in combination with or in place of detection electrodes (228, 230) described above.

Ablation system processor (252) may be configured to modulate the ablation energy provided to ablation element (210) from ablation energy source (250) based on the condition of the nerve as detected by nerve sensor (228, 230, 232). For instance, processor (252) may monitor the deteriorating condition of the nerve, as indicated by a progressively weakening signal received by second detection electrode (230) and/or by a progressively increasing temperature detected by temperature sensor (232). In response, ablation system processor (252) may progressively decrease the supplied ablation energy as the nerve approaches a fully ablated state. Upon determining that the nerve is fully ablated, via signals provided by nerve sensor (228, 230, 232), ablation system processor (252) may automatically cease application of ablation energy without further input provided by the surgeon.

As shown in FIG. 5, navigation sensor (240) of the present example is provided in the form of an electrically conductive coil (e.g., a metallic wire wrapped helically into a coil configuration) arranged within an interior of probe (204) about the longitudinal axis of surgical instrument (200). While navigation sensor (240) is shown arranged within a distal end of probe shank (206), it will be appreciated that navigation sensor (240) may be arranged within various other portions of probe (204) in other examples, such as within distal tip (208). Additionally, while navigation sensor (240) is shown arranged about the longitudinal axis of instrument (200), sensor (240) may be positioned in various other orientations in other examples. For instance, navigation sensor (240) may be positioned about an axis that extends obliquely relative to the longitudinal axis of instrument (200), for example as disclosed in U.S. patent application Ser. No. 15/923,164, entitled "Navigation Instrument With Obliquely Oriented Sensing Coil," filed Mar. 19, 2018, now abandoned, the disclosure of which is incorporated by reference herein. In other examples, surgical instrument (200) may include two or more navigation sensors, each of which may comprise an electrically conductive coil similar to that of navigation sensor (240), and each of which may be oriented about a different respective axis. For instance, two or three coil sensors may be used, with the sensors being oriented about respective axes that are orthogonal to each other.

As described above, navigation sensor (240) is operable to communicate with navigation system processor (108) to track a location of probe (204) within a patient during a surgical procedure. In particular, the presence of navigation sensor (240) in the alternating electromagnetic field generated by field generators (106) induces an electrical current in the conductive coil of sensor (240), which is communicated proximally to navigation system processor (108) as a signal. Processor (108) then executes an algorithm based on these signals to determine a location of navigation sensor (240), and thus a distal end of probe (204), within the patient. Processor (108) communicates with display (114) to display in real-time a location a location of probe (204) within the patient, so the surgeon may confidently track the location of probe (204) during a surgical procedure.

As shown schematically in FIG. 5, navigation sensor (240) communicates with navigation system processor (108) via a first communication member (242) that extends longitudinally through surgical instrument (200). Nerve sensor (228, 230, 232) communicates with ablation system processor (252) via a second communication member (244). Additionally, RF electrodes (222, 224) communicate with RF energy source (250) via a third communication member (246). It will be appreciated that any one or more of communication members (242, 244, 246) may comprise a plurality of individual communication elements such as conductive wires, optical pathways, or fluid pathways for example, suitable to establish communication between probe (204) and the appropriate member of system (100). In some examples, communication members (242, 244, 246) may communicate with the respective navigation system processor (108), ablation system processor (252), and/or ablation energy source (250) via communication unit (116), described above.

C. Exemplary Vidian Neurectomy Procedures

Figure 6A:
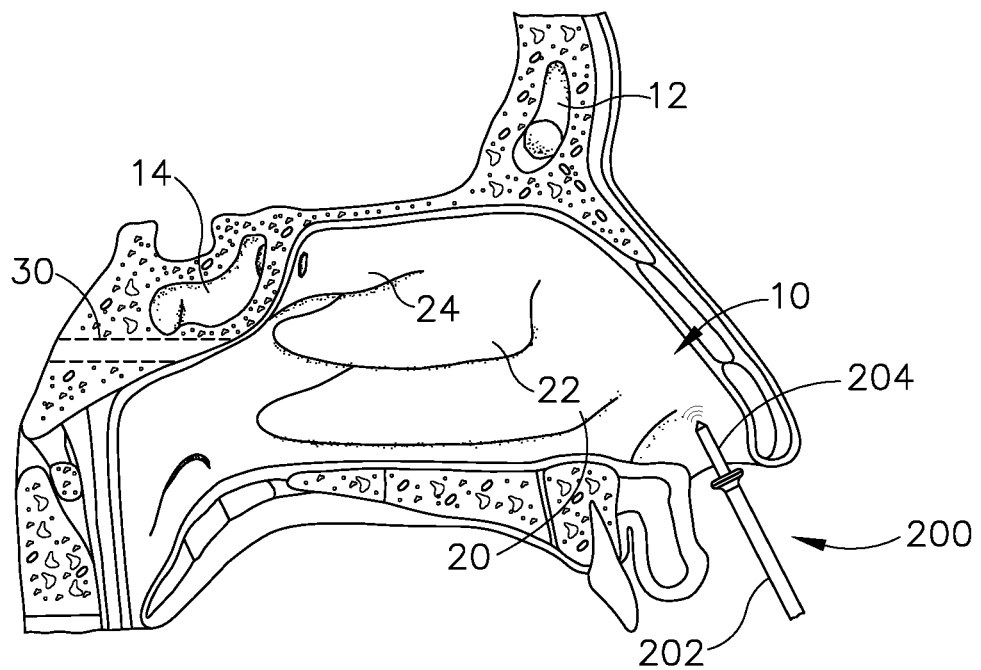
FIG. 6A depicts a schematic left sagittal view of a portion of a patient's head, showing a distal end of the surgical instrument of FIG. 3 being inserted into the nasal cavity.
Figure 6B:
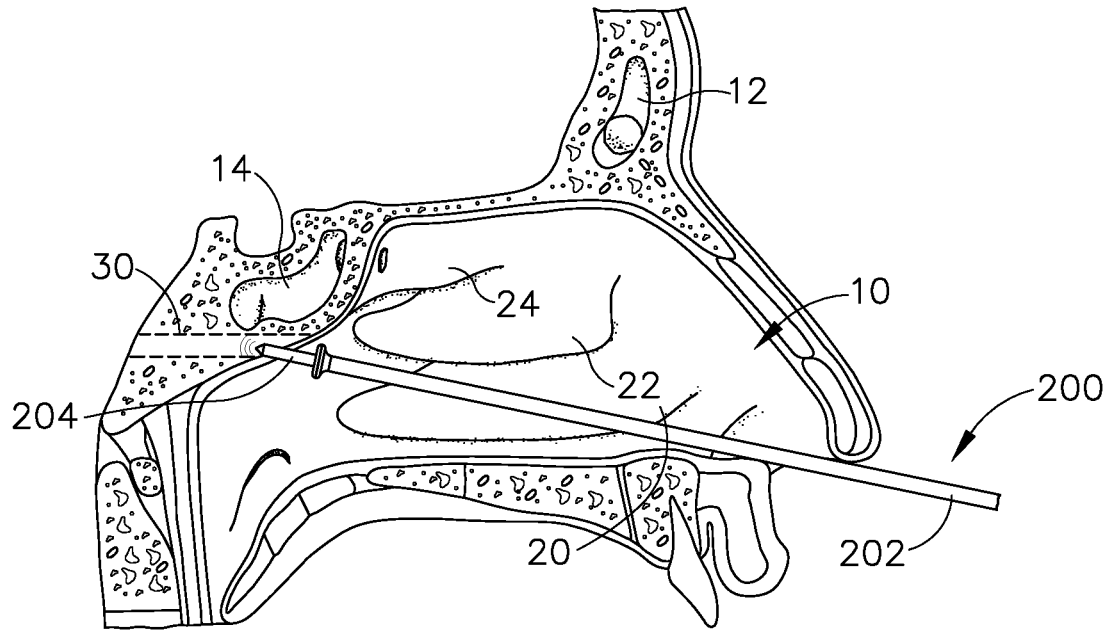
FIG. 6B depicts a schematic left sagittal view of the patient's head of FIG. 6A, showing the probe of the surgical instrument being positioned relative to the vidian canal.

FIGS. 6A-6E show steps of an exemplary vidian neurectomy procedure performed on a patient using surgical instrument (200) described above. As shown in FIG. 6A, the distal end of instrument (200) is inserted through the patient's nostril and into nasal cavity (10). As shown in FIG. 6B, instrument probe (204) is advanced through nasal cavity (10) in a posterior direction, while the surgeon monitors the location of probe (204) within the patient via display (114) of navigation system (100). As described above, navigation sensor (240) interacts with the electromagnetic field generated by field generators (106) of navigation system (100) to generate and communicate to navigation system processor (108) signals indicating the location of probe (204) within the patient. In this manner, the surgeon may monitor the location of probe (204) on display (114) to thereby guide probe (204) toward a selected portion of the patient's vidian canal (30), depicted schematically.

Figure 6E:
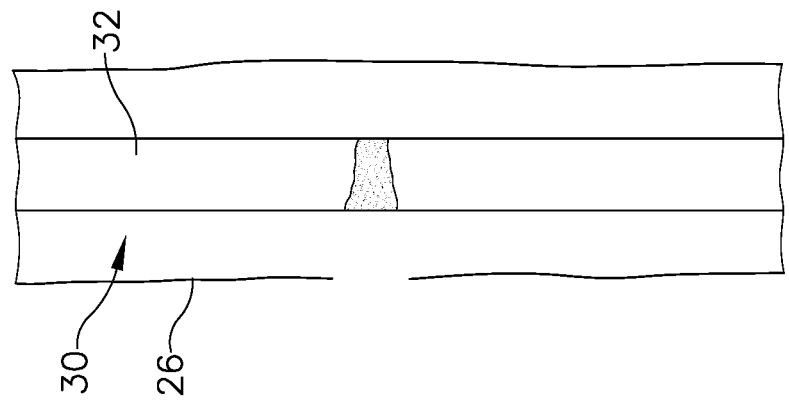
FIG. 6E depicts a schematic top view of the anatomy of FIG. 6D, showing the vidian nerve following ablation by the ablation element of the instrument probe.
Figure 6D:
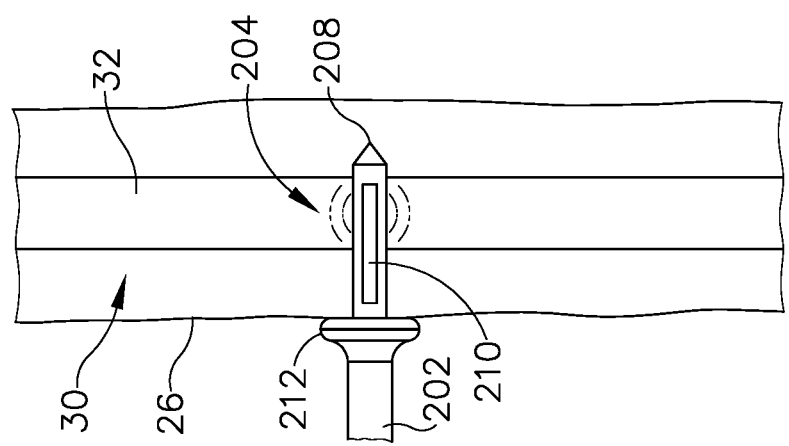
FIG. 6D depicts a schematic top view of the anatomy of FIG. 6C, showing the probe puncturing through a side portion of the vidian canal so the ablation element engages the vidian nerve along a first axis.
Figure 6C:
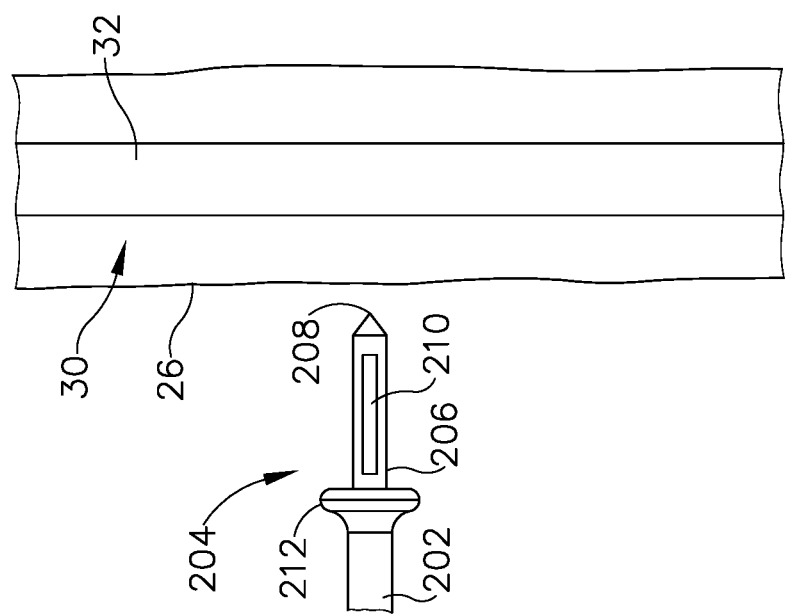
FIG. 6C depicts a schematic top view of the vidian canal and vidian nerve of FIG. 6B, showing the instrument probe positioned adjacent to a side portion of the vidian canal.

FIG. 6C shows instrument probe (204) positioned along a side portion of vidian canal (30), which contains vidian nerve (32), such that probe (204) extends along an insertion axis that is generally perpendicular to a longitudinal axis of vidian canal (30). Alternatively, probe (204) may be otherwise oriented transversely (e.g., obliquely) relative to the longitudinal axis of vidian canal (30). As shown in FIG. 6D, the surgeon advances surgical instrument (200) further into the patient so that distal tip (208) of probe (204) punctures through a tissue surface (26) that defines a wall of vidian canal (30). Probe (204) advances into vidian canal (30) until stop collar (212) abuts tissue surface (26), thereby preventing further advancement of probe (204) into vidian canal (30). As described above, probe (204) of the present example extends distally from stop collar (212) by a suitable distance (X) such that probe (204) is suitably positioned to engage vidian nerve (32) in vidian canal (30) when stop collar (212) abuts tissue surface (26).

As shown schematically in FIG. 6D, ablation element (210) of probe (204) is activated to deliver ablation energy to vidian nerve (32) to thereby ablate nerve (32). As described above, ablation element (210) of the present example is in the form of a pair of RF electrodes (222, 224) operable to ablate nerve (32) with bipolar RF energy. Once ablation system processor (252) detects that vidian nerve (32) has been fully ablated, processor (252) may automatically deactivate application of ablation energy, or otherwise provide an indication to the surgeon that ablation is complete so the surgeon may manually cease application of ablation energy. As shown in FIG. 6E, vidian nerve (32) is now fully ablated and the surgeon withdraws surgical instrument from the patient through nasal cavity (10). While the exemplary procedure shown depicts full ablation of vidian nerve (32), it will be appreciated that surgical system (100) may be operated to perform only partial ablation of vidian nerve (32) in other instances.

Figure 7C:
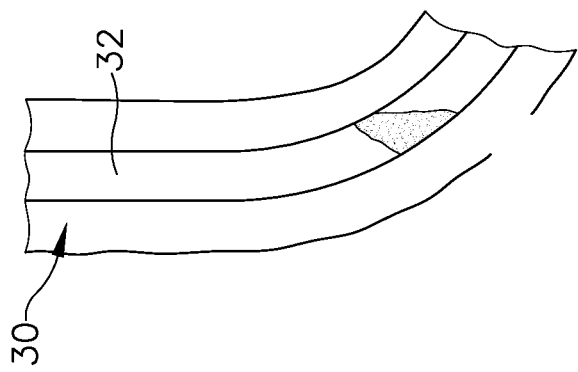
FIG. 7C depicts a schematic top view of the anatomy of FIG. 7B, showing the vidian nerve following ablation by the ablation element of the instrument probe.
Figure 7B:
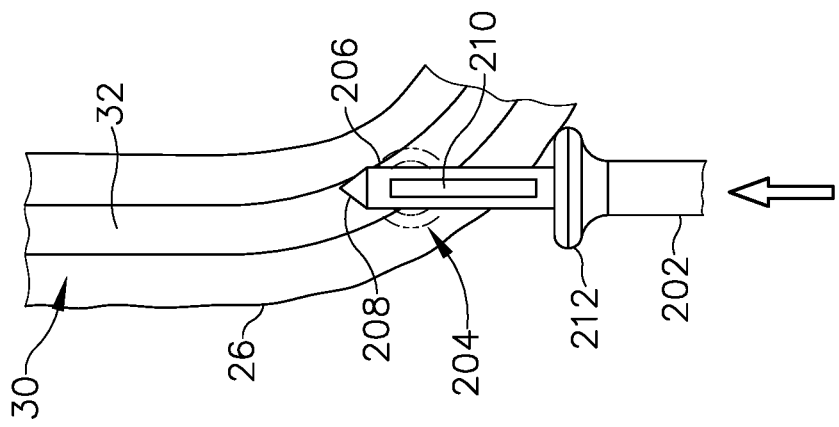
FIG. 7B depicts a schematic top view of anatomy of FIG. 7A, showing the probe puncturing through an end portion of the vidian canal so the ablation element engages the vidian nerve along a second axis.
Figure 7A:
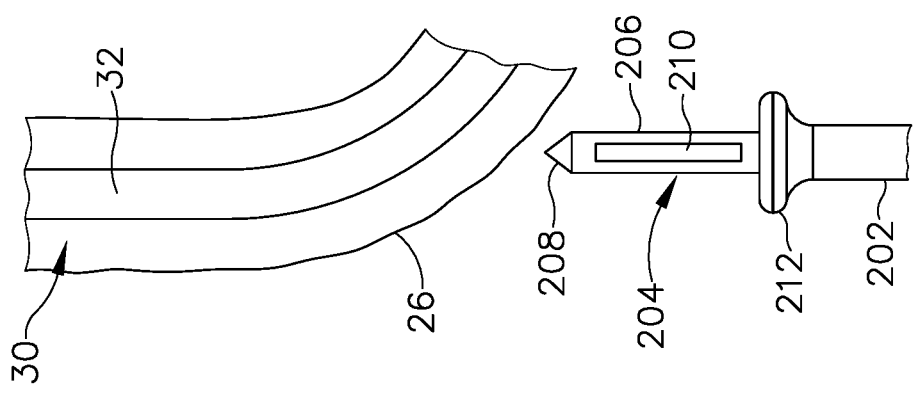
FIG. 7A depicts a schematic top view of the vidian canal and vidian nerve of FIG. 6A, showing the instrument probe positioned adjacent to an end portion of the vidian canal in an exemplary alternative surgical procedure.

FIGS. 7A-7C show an exemplary alternative vidian neurectomy procedure that is similar to the vidian neurectomy procedure shown in FIGS. 6C-6E, except as otherwise described. In particular, instrument probe (204) is guided by the surgeon along an insertion axis that extends generally parallel to the longitudinal axis of vidian canal (30) and vidian nerve (32), such that distal tip (208) punctures through an end portion of vidian canal (30). As shown in FIG. 7B, probe (204) thus engages vidian nerve (32) along the insertion axis such that probe (204) extends through and generally parallel with vidian nerve (32). Ablation element (210) of probe (204) is then activated in the manner described above to ablate vidian nerve (32), as shown in FIG. 7C. It will be appreciated that surgical instrument (200) may be positioned relative to vidian nerve (32) or other nerves of a patient in various other orientations suitable to provide full or partial ablation of the nerve as desired.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a shaft; (b) a probe extending distally from a distal end of the shaft, wherein the probe comprises: (i) a distal tip, wherein the distal tip is configured to puncture a tissue surface to enter a nerve canal of a patient, and (ii) an ablation element, wherein the ablation element is operable to ablate a nerve located within the nerve canal; and (c) a stop element arranged proximally of the distal tip, wherein the stop element is configured to abut the tissue surface punctured by the distal tip.

Example 2

The surgical instrument of Example 1, wherein the distal tip is configured to puncture a tissue surface to enter a vidian nerve canal of a patient, wherein the ablation element is operable to ablate a vidian nerve located within the vidian nerve canal.

Example 3

The surgical instrument of any of the previous Examples, wherein the probe and the stop element are sized to be inserted into a nasal cavity of the patient.

Example 4

The surgical instrument of any of the previous Examples, wherein the probe has a length of approximately 8 millimeters.

Example 5

The surgical instrument of any of the previous Examples, wherein the stop element is arranged at a proximal end of the probe.

Example 6

The surgical instrument of any of the previous Examples, wherein the stop element comprises a collar.

Example 7

The surgical instrument of any of the previous Examples, wherein the ablation element comprises an RF electrode, wherein the RF electrode is operable to deliver RF energy to the nerve to thereby ablate the nerve.

Example 8

The surgical instrument of any of the previous Examples, further comprising a navigation sensor, wherein the navigation sensor is operable to generate a signal corresponding to a location of the probe within the patient.

Example 9

The surgical instrument of any of Example 8, wherein the navigation sensor is located within the probe.

Example 10

The surgical instrument of any of Examples 8 through 9, wherein the navigation sensor comprises an electrically conductive coil.

Example 11

The surgical instrument of any of the previous Examples, further comprising a nerve sensor, wherein the nerve sensor is operable to detect a condition of the nerve treated by the probe.

Example 12

The surgical instrument of Example 11, wherein the nerve sensor is carried by the probe.

Example 13

The surgical instrument of any of Examples 11 through 12, wherein the nerve sensor comprises a temperature sensor.

Example 14

The surgical instrument of any of Examples 11 through 12, wherein the nerve sensor comprises a pair of detection electrodes, wherein the detection electrodes are operable to direct a neuro-stimulating signal through the nerve to thereby detect presence of the nerve before ablation of the nerve is complete.

Example 15

A surgical system comprising: (a) the surgical instrument of any of Examples 11 through 14; (b) an ablation energy source operable to deliver ablation energy to the ablation element; and (c) a processor, wherein the processor is in communication with the nerve sensor and with the ablation energy source, wherein the processor is operable to modulate the ablation energy delivered from the ablation energy source to the ablation element based on the condition detected by the nerve sensor.

Example 16

A surgical system comprising: (a) a surgical instrument, wherein the surgical instrument comprises: (i) a shaft, and (ii) a probe extending distally from a distal end of the shaft, wherein the probe comprises: (A) a distal tip, wherein the distal tip is configured to puncture tissue to enter a nerve canal of a patient, (B) an ablation element, wherein the ablation element is operable to ablate a nerve located within the nerve canal, and (C) a navigation sensor, wherein the navigation sensor is operable to generate a signal corresponding to a location of the probe within the patient; and (b) a processor, wherein the processor is in communication with the navigation sensor, wherein the processor is operable to track a location of the probe within the patient based on the signal generated by the navigation sensor.

Example 17

The surgical system of Example 16, wherein the ablation element comprises a pair of RF electrodes, wherein the RF electrodes are operable to deliver bipolar RF energy to the nerve to thereby ablate the nerve.

Example 18

The surgical instrument of any of Examples 16 through 17, wherein the navigation sensor comprises an electrically conductive coil.

Example 19

A method of performing a vidian neurectomy on a patient with a surgical instrument having a shaft, a probe with an ablation element, and a stop element, the method comprising: (a) inserting a distal portion of the surgical instrument into the nasal cavity of the patient; (b) puncturing through a tissue surface and into the vidian canal with a distal tip of the probe; (c) advancing the probe into the vidian canal until the stop element abuts the tissue surface; (d) ablating at least a portion of the vidian nerve in the vidian canal with the ablation element; and (e) withdrawing the surgical instrument from the patient through the nasal cavity.

Example 20

The surgical instrument of Example 19, wherein the surgical instrument includes a navigation sensor, wherein the method further comprises tracking a location of the probe within the patient based on a signal provided by the navigation sensor.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of performing a vidian neurectomy on a patient with a surgical instrument having a fully rigid shaft extending along a longitudinal axis, a probe with an ablation element, and a stop element extending radially outwardly relative to the shaft and circumferentially about the longitudinal axis, the method comprising:
   (a) inserting a distal portion of the surgical instrument into a nasal cavity of the patient, wherein the act of inserting the distal portion of the surgical instrument into the nasal cavity is performed with the shaft in a straight state and with the ablation element exposed to the nasal cavity of the patient;
   (b) puncturing through a tissue surface and into a vidian canal with a distal tip of the probe, wherein the act of puncturing through the tissue surface and into the vidian canal with the distal tip is performed while maintaining the shaft in the straight state, wherein the act of puncturing through the tissue surface and into the vidian canal with the distal tip includes applying a distally-directed puncturing force to the shaft;
   (c) advancing the probe into the vidian canal until the stop element abuts the tissue surface, wherein the act of advancing the probe into the vidian canal is performed with each of the probe and the shaft extending along an insertion axis that is perpendicular to a longitudinal axis of the vidian canal;

(d) arresting advancement of the probe into the vidian canal in response to the stop element abutting the tissue surface, (e) ablating at least a portion of a vidian nerve in the vidian canal with the ablation element while the stop element abuts the tissue surface, wherein the ablation element is proximally spaced apart from the distal tip; and (f) withdrawing the surgical instrument from the patient through the nasal cavity.

2. The method of claim 1, wherein the surgical instrument includes a navigation sensor, wherein the method further comprises tracking a location of the probe within the patient based on a signal provided by the navigation sensor.

3. The method of claim 1, wherein the tissue surface defines a wall of the vidian canal.

4. The method of claim 1, wherein the ablation element comprises an RF electrode, wherein the act of ablating at least a portion of the vidian nerve in the vidian canal includes delivering RF energy to the vidian nerve with the RF electrode.

5. The method of claim 1, wherein the surgical instrument includes a nerve sensor, wherein the method further comprises detecting a condition of the vidian nerve with the nerve sensor.

6. The method of claim 5, wherein the nerve sensor comprises a pair of detection electrodes, wherein the act of detecting the condition of the vidian nerve includes directing a neuro-stimulating signal through the vidian nerve with the nerve sensor to thereby detect a presence of the vidian nerve before the act of ablating is complete.

7. A method of performing a vidian neurectomy on a patient with a surgical instrument having a fully rigid shaft, a probe with an ablation element, and a stop element, the method comprising:

(a) inserting a distal portion of the surgical instrument into a nasal cavity of the patient, wherein the act of inserting the distal portion of the surgical instrument into the nasal cavity is performed with the ablation element exposed to the nasal cavity of the patient;

(b) puncturing through a tissue surface and into a vidian canal at only a single location with only a single distal tip of the probe, wherein the act of puncturing through the tissue surface and into the vidian canal with the single distal tip includes applying a distally-directed puncturing force to the shaft while maintaining the shaft in a straight state;

(c) advancing the probe into the vidian canal until the stop element abuts the tissue surface, wherein the act of advancing the probe into the vidian canal is performed with each of the probe and the shaft extending along an insertion axis that is one of oblique or parallel relative to a longitudinal axis of the vidian canal;

(d) ablating at least a portion of a vidian nerve in the vidian canal with the ablation element; and (e) withdrawing the surgical instrument from the patient through the nasal cavity.

8. The method of claim 7, wherein the single distal tip is closed.

9. A method of performing a vidian neurectomy on a patient with a surgical instrument having (i) a shaft, (ii) a probe with (A) a shank having a solid cylindrical outer surface, (B) a closed distal tip, and (C) an ablation element arranged on the shank, and (iii) a stop element, the method comprising:

(a) inserting a distal portion of the surgical instrument into a nasal cavity of the patient;

(b) puncturing through a tissue surface and into a vidian canal with only the closed distal tip of the probe;

(c) advancing the probe into the vidian canal until the stop element abuts the tissue surface;

(d) ablating at least a portion of a vidian nerve in the vidian canal with the ablation element; and (e) withdrawing the surgical instrument from the patient through the nasal cavity.

10. The method of claim 9, wherein the act of advancing the probe into the vidian canal is performed with the probe extending along an insertion axis that is one of oblique or parallel relative to a longitudinal axis of the vidian canal.

11. The method of claim 9, wherein the act of puncturing through the tissue surface and into the vidian canal with the closed distal tip includes applying a distally-directed puncturing force to the shaft while maintaining the shaft in a straight state.

* * * * *